United States Patent
Meyerhoff et al.

(10) Patent No.: US 6,908,542 B2
(45) Date of Patent: Jun. 21, 2005

(54) ROTATING POTENTIOMETRIC ELECTRODE

(75) Inventors: Mark E. Meyerhoff, Ann Arbor, MI (US); Qingshan Ye, Plymouth, MN (US)

(73) Assignee: The Regents of the University of Michigan, Ann Arbor, MI (US)

( * ) Notice: Subject to any disclaimer, the term of this patent is extended or adjusted under 35 U.S.C. 154(b) by 347 days.

(21) Appl. No.: 10/013,301

(22) Filed: Dec. 7, 2001

(65) Prior Publication Data

US 2002/0125132 A1 Sep. 12, 2002

Related U.S. Application Data

(60) Provisional application No. 60/254,496, filed on Dec. 8, 2000.

(51) Int. Cl.[7] ............................................. G01N 27/333
(52) U.S. Cl. ........................................ 205/789; 204/418
(58) Field of Search ................................ 204/416, 418; 205/789, 790

(56) References Cited

U.S. PATENT DOCUMENTS

| | | | |
|---|---|---|---|
| 5,236,570 A | 8/1993 | Ma et al. | 204/403.06 |
| 5,453,171 A | 9/1995 | Ma et al. | 257/414 |
| 5,607,567 A | 3/1997 | Yun et al. | 204/418 |

OTHER PUBLICATIONS

Lukashev, "Polarizatio haracteristics of monopolar ionite membranes," Russian Journal of Environmental Development, Moscow, Russia (2000), 36(4), 367–372, Apr. 2000.*
Pages 16 and 25 of the Orion 1997 Laboratory products and Electrochemistry Handbook.*
Ramamurthy, et al., "Determination of Low–Molecular-Weight Heparins and Their Binding to Protamine and a Protamine Analog Using Poly–Sensitive Membrance Electrodes", Analytical Biochemistry, vol. 266, No. 1, Jan. 1, 1999, pp. 116–124.

Wingard, Lemuel B., et al., "Immobilized Glucose Oxidase in the Potentiometric Detection of Glucose", Applied Biochemistry and Biotechnology, vol. 9, Feb. 1994, pp. 95–104.

Meyerhoff and Ye, "Rotating Electrode Potentionmetry: Lowering the Detection Limits of Nonequilibrium Polyion-Sensitive Membrane Electrodes", Analytical Chemistry, vol. 73, pp. 332–336.

Fu, et al., Response Mechanism of Polymer MembraneBased Potentiometric Polyion Sensors, Anal. Chem., vol. 66, p. 2250–2259 (1994).

Mathison, et al., Renewable ph Cross–Sensitive Potentiometric Heparin Sensors with Incorporated Electrically Charged H+ Ionophores, Anal. Chem., vol. 71, pp. 4613–4621 (1999).

* cited by examiner

Primary Examiner—Alex Noguerola
(74) Attorney, Agent, or Firm—Dierker and Associates, P.C.

(57) ABSTRACT

A rotating electrode configuration lowers the detection limits of polyion-sensitive membrane electrodes. Planar potentiometric polycation and polyanion-sensitive membrane electrodes were prepared by incorporating tridodecylmethylammonium chloride and calcium dinonylnaphthalene sulfonate, respectively, into plasticized PVC or polyurethane membranes, and mounting discs of such films on an electrode body housed in a rotating disk electrode apparatus of the type used in voltammetry. Due to the unique non-equilibrium response mechanism of such sensors, rotation of the polyion-sensitive membrane electrodes at 5000 rpm resulted in an enhancement in the detection limits toward heparin (polyanion) and protamine (polycation) of at least 1 order of magnitude (to 0.01 U/ml for heparin; 0.02 μg/ml for protamine) over that observed when the EMF responses of the same electrodes were assessed using a stir-bar to achieve convective mass transport.

11 Claims, 4 Drawing Sheets

ROTATING POTENTIOMETRIC ELECTRODE

CROSS-REFERENCE TO RELATED INVENTIONS

This application claims the benefit of; U.S. Provisional Patent Application Ser. No. 60/254,496, filed Dec. 8, 2000.

GOVERNMENT RIGHTS

This invention was made under contract awarded by the National Institutes of Health, Contract Number GM28882. The government has certain rights in the invention.

BACKGROUND OF THE INVENTION

1. Field of the Invention

This invention relates generally to polyion-sensitive membrane electrodes, and more particularly, to a unique rotating potentiometric polyion-sensitive membrane electrode, and methods of using same, using membranes of the type having a non-equilibrium response mechanism.

2. Description of the Related Art

Recently, it has been discovered that specially formulated polymer membranes doped with appropriate lipophilic ion-exchangers yield large and reproducible potentiometric responses toward various biomedically important polyanions (e.g., heparin, DNA, and polyphosphates) and polycations (e.g., protamine and polyarginine) at $\mu$g/ml levels in the presence of physiological concentrations of common inorganic ions. Examples of such polyion-sensitive, or polyion-responsive, membrane electrodes are described in U.S. Pat. Nos. 5,453,171; 5,236,570; and 5,607,567, the disclosures of which are incorporated herein by reference.

The EMF response of these so-called polyion-sensitive membrane electrodes (PSEs) has been ascribed to the establishment of a non-equilibrium, steady-state ion-exchange process that occurs at the membrane/sample interface. This exchange occurs because of the very favorable extraction of the analyte polyion into the organic membrane phase by cooperative ion-pairing with the lipophilic ion-exchange species. A detailed description of the fundamental response mechanism of the PSEs is found in Fu, et al., *Anal. Chem.*, Vol. 66, pages 2250–2259 (1994), the disclosure of which is incorporated herein by reference.

The polyanion-sensitive electrode devices have many useful bioanalytical applications several of which are described below. For example, accurate determinations of the level of the anticoagulant heparin in undiluted whole blood have been achieved via a simple potentiometric titration using protamine as the titrant and a polycation-sensitive membrane electrode as the end-point detector. Both polycation and polyanion-sensitive membrane electrodes have been shown to be useful as detectors for the determination of certain enzyme activities that cleave larger polyionic substrate molecules into smaller fragments of lower charge and molecular weight. Enzyme analysis applications rely on the fact that these devices exhibit much less EMF response to lower molecular weight polyions, owing to a significant decrease in the strength of cooperative ion pairing between the low molecular weight polyion and the lipophilic ion-exchanger within the membrane phase. Very recently, PSEs have been used as detectors in the development of a novel, non-separation, competitive binding immunoassay scheme in which synthetic polycationic peptides are employed as labels.

Given the large number of potential applications of PSEs, it would be desirable to further enhance the sensitivity of these electroanalytical devices. Some progress has been made in this regard. Previously, it had been discovered that lowering the plasticizer content in the polymer membrane matrix improves the sensitivity of the PSEs by reducing the diffusion coefficient of the polyion-exchanger complex. Further, it was discovered that the shape of the electrode affects the sensitivity of PSEs. A cylindrical membrane electrode design was found to be slightly more sensitive than a planar membrane configuration owing to the enhanced mass transfer of the polyion to the membrane surface by cylindrical diffusion versus planar diffusion. It was also noted earlier that stirring the sample solution, illustratively with a stir-bar, results in an improvement in analyte sensitivity for PSEs relative to the sensitivity in a non-stirred solution. Each of these observations, taken together, also helped to determine, definitively, that PSEs have an operative non-equilibrium response mechanism.

There is, however, a need for additional improvements in polyion membrane electrode sensitivity. Due to the non-equilibrium response mechanism of PSEs, improvements in sensitivity can be made by employing a method to further enhance mass transfer of the analyte polyion to the membrane/sample interface in a controllable manner. Rotating electrode voltammetry and amperometry are well-established hydrodynamic methods that yield enhanced mass transfer of analyte as a function of the rotation speed of a planar working electrode. However, rotating electrode technology has not heretofore been applied to potentiometry.

It is, therefore, an object of this invention to provide a polyion-sensitive membrane electrode with improved sensitivity.

It is another object of this invention to provide a novel polyion-sensitive membrane electrode with improved sensitivity by employing a rotating electrode to enhance mass transfer of the analyte to the membrane/sample interface.

SUMMARY OF THE INVENTION

The foregoing and other objects are achieved by this invention which provides a polyion-sensitive membrane electrode assembly wherein sensitivity is improved by rotating a potentiometric polyion-responsive membrane electrode in the sample solution. When the polyion-sensitive membrane has a non-equilibrium response mechanism, rotation will improve mass transfer of polyion to the membrane surface. Relatively low rotational speed, illustratively from about 500 rpm up to about 5000–6000 rpm, improves sensitivity with a linear relationship being found between the observed sensitivity and $\omega^{-1/2}$ (where $\omega$ is the rotating angular frequency), and $C_{1/2}$, the polyion concentration corresponding to one-half the total maximum $\Delta$EMF response toward the polyion species.

In preferred embodiments of the invention, the polyion-sensitive membranes are selectively responsive to polycationic macromolecules such as protamine, and polyanionic macromolecules, such as heparin, depending upon the formulation of the polymeric membrane matrix. In general, the polyion-responsive membrane comprises, in admixture, a polymeric matrix material, lipophilic cation- or anion-exchange material, and, optionally, a plasticizer.

In addition to the polyion-sensitive membranes used in the experiments presented herein, suitable protamine-responsive membrane materials are set forth in U.S. Pat. No. 5,607,567 and suitable heparin-responsive membranes are set forth in U.S. Pat. No. 5,236,570, for example.

In an illustrative device embodiment, a rotating polyionic membrane electrode assembly includes, in one embodiment, a rotatable housing having a bore through the central axis thereof. A polyion-responsive membrane is disposed on one end of the housing, so that the rotation of the housing rotates the membrane. The membrane seals a filling solution, or a reference solution, inside the housing and contacts the sample solution external to the housing. An internal reference electrode extends through the bore of the housing and is arranged so that one end of the internal reference electrode is disposed in the reference solution. The other end of the internal reference electrode is connected to a high impedance voltmeter. An external electrode is also connected to the voltmeter.

It is important that the internal reference electrode be insulated from the housing. An insulating tube or sheath, such as polyethylether ketone (PEEK) tubing, can be used to minimize electrical noise during high-speed rotation. The tubing also prevents any electrical contact between the internal electrode and other elements of rotating housing. In addition, the internal reference electrode needs to be mechanically isolated from the rotating housing to avoid any vibration coupling from the rotator.

In the device embodiment described herein, the entire housing rotates, including the polyion-sensitive membrane. Alternative embodiments can be devised, however, wherein the housing is stationary and only the polyion-sensitive membrane rotates.

In a method of use embodiment, the concentration of a polyionic macromolecule in a liquid medium is measured as a function of its potentiometric response by:

(a) bringing a polyion-responsive membrane electrode into contact with the liquid medium containing an unknown quantity of polyionic macromolecule analyte, the polyion-responsive membrane comprising a polymeric matrix material which has a non-equilibrium response mechanism to the analyte;

(b) rotating the polyion-responsive membrane in the liquid medium; and (c) measuring a potentiometric response which is indicative of the concentration of analyte in the liquid medium.

In contrast to conventional ion-selective membrane electrodes that operate under equilibrium conditions, the EMF responses of PSEs are generated by a non-equilibrium quasi-steady-state ion exchange process that occurs at the membrane/sample interface. It has been shown that this steady-state occurs when the flux of polyions diffusing from the sample phase to the membrane surface equals the flux of the polyion-ion-exchanger ion pair that diffuses away from the membrane surface into the bulk of the polymer membrane. At low polyion concentrations, where a significant fraction of the original ion-exchanger counterions (e.g., inorganic cations for calcium dinonylnaphthalene sulfonate-based polycation sensors and inorganic anions for tridodecylmethylammonium chloride-based polyanion sensors) are still present at the outer surface of the organic membrane, the ΔAEMF observed under such conditions can be described as follows:

$$\Delta EMF = \pm \left(\frac{RT}{F}\ln\left(1 - \frac{z}{R_T}\frac{D_a d_m}{D_m d_a}c_{poly,bulk}\right)\right) \quad \text{Eqn. (1)}$$

where, $R_T$ is the total concentration of ion-exchanger sites within the membrane phase; z is the charge number on the analyte polyion; $D_a$ and $D_m$ are the diffusion coefficients of polyion in the aqueous and membrane phases, respectively; $\delta^a$ and $\delta_m$ are the diffusion layer thicknesses for the polyion in the aqueous phase and the membrane phase, respectively; $C_{poly,bulk}$ is the bulk concentration of polyions in the sample solution; + is for the polyanion response and − is for the polycation response; T is the temperature in Kelvin; and R and F are the gas and Faraday constants, respectively.

From Eqn. 1, it is clear that, to achieve the same ΔEMF response, a simple way to lower detection limits toward a given polyion (i.e., to achieve a smaller $C_{poly,bulk}$) is to reduce the diffusion layer thickness in the aqueous phase ($\delta_a$) while keeping all the other parameters constant. One effective approach for reproducibly controlling and further reducing the diffusion layer thickness is to rotate the membrane electrode.

For a disk electrode, $\delta_a$ is related to the angular rotating frequency ω as follows:

$$\delta = 1.61 D_a^{1/3} \nu^{1/6} \omega^{-1/2} \quad \text{Eqn. (2)}$$

where ν is the kinematic viscosity (defined as the ratio of the normal viscosity η to the solution density ρ). In accordance with Eqn. (1), a decrease of 10-fold in $\delta_a$ should require 10-fold lower polyion concentration to yield the same EMF response.

The validity of this concept has been demonstrated in both polyanion and polycation-sensitive membrane electrodes in the experimental results presented hereinbelow.

BRIEF DESCRIPTION OF THE DRAWING

Comprehension of the invention is facilitated by reading the following detailed description, in conjunction with the annexed drawing, in which.

DETAILED DESCRIPTION OF THE INVENTION

Membrane and PSE Electrode Preparation

In a specific illustrative embodiment of the invention, polyanion-sensitive membranes, specifically heparin-sensitive membranes, were prepared by a cocktail solution casting method as described, for example, in Mathison, et al., *Anal. Chem.*, Vol. 71, pages 4614–4621 (1999) or any of the patents referenced herein. The cocktail solution was prepared by dissolving the appropriate amounts of membrane components (polymer, plasticizer and ion-exchanger) into tetrahydrofuran (THF). The membranes were cast in a mold to a final thickness of about 150 μm and contained 1 wt % tridodecylmethylammonium chloride (TDMAC), 33 wt % dioctyl sebacate (DOS) and 66 wt % poly(vinyl chloride) (PVC).

In another specific illustrative embodiment, polycation-sensitive membranes, specifically protamine-sensitive membranes, were made by the same method but with the following polymeric membrane matrix composition: 1 wt % calcium dinonylnaphthalene sulfonate (DNNS), 49 wt % nitrophenyloctyl ether (NPOE) and 49 wt % polyurethane (M48 supplied by Medtronic Inc., Minneapolis, Minn.).

Disks of the polyion-sensitive membranes were cut with a cork-borer (o.d. 7.0 mm) and were glued at one end of 1-cm long Tygon brand flexible tubes (i.d. 4.2 mm, o.d. 7.35 mm, Fisher Scientific, Pittsburgh, Pa.) to form a housing for the reference solution.

The Rotating PSE System

Figure 1:
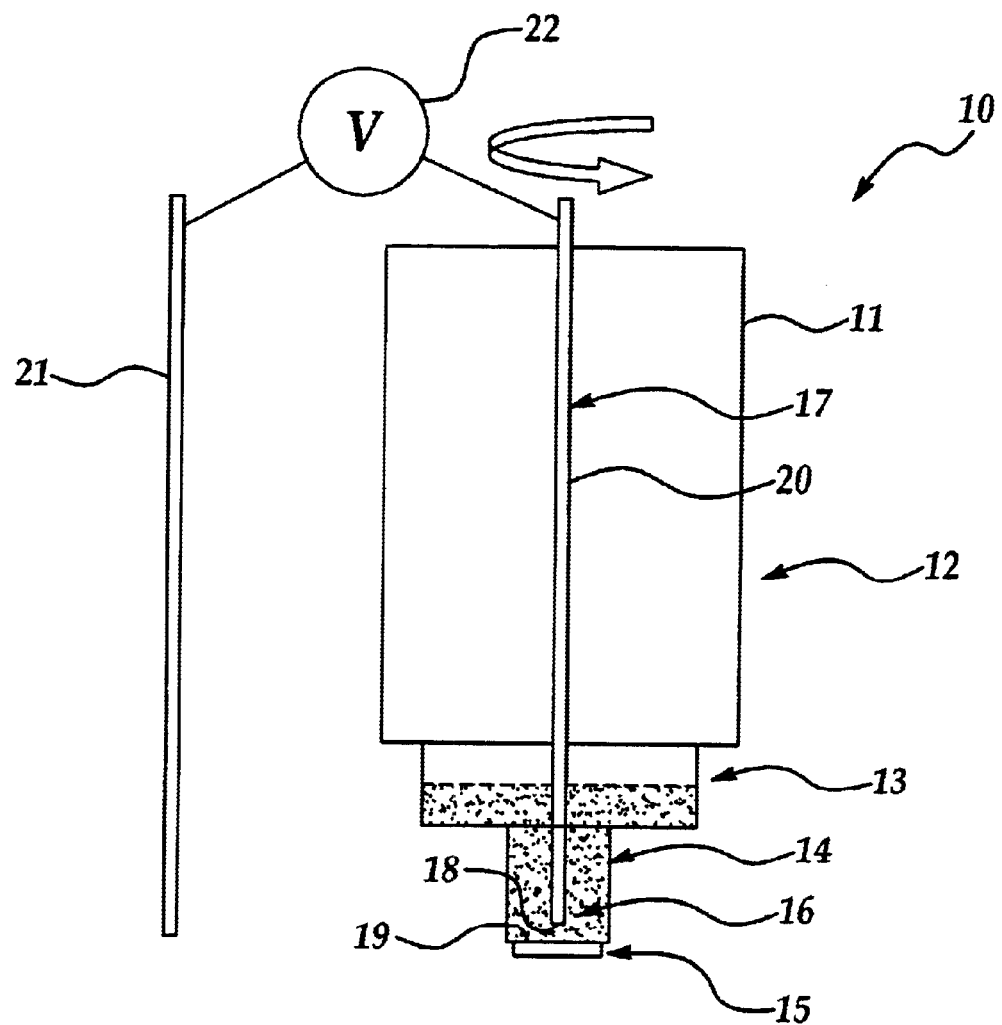
FIG. 1 is a schematic diagram of a rotating polyion-sensitive potentiometric membrane electrode in accordance with the invention.

FIG. 1 is a schematic diagram of a practical embodiment of a rotating polyion-sensitive potentiometric membrane electrode 10 in accordance with the invention. In the specific illustrative embodiments described herein, a rotating electrode, commercially available from Pine Instrument Co., Grove City, Pa., (Analytical Rotator model ASR with an ASR motor control box (1000 rpm/V, 200 to 10,000 rpm range) has been adapted to form a rotatable housing 11 by using a 2-cm long connecting tube 13 made of black Delrin plastic (McMaster-Carr, Cleveland, Ohio) to connect the rotator 12 and a 1-cm long Tygon tube 14 with the polyion-sensitive membrane disk 15 glued at the distal end. Both the Delrin tube and the Tygon tube were filled with an internal filling, or reference, solution 16. In this case, reference solution 16 is tris[(hydroxy methyl)aminomethane] (Tris) buffer with 0.12 M NaCl. An internal reference electrode 17 was inserted through the central void space of rotator 12 and so that a tip 18 extends to near the inner surface 19 of the polyion-sensitive membrane, as shown in FIG. 1. Internal reference electrode 17 was made with a thin silver wire (o.d., 0.076 mm, Medwire, Mt. Vernon, N.Y.) inserted through an insulating sheath 20, which in this embodiment is a PEEK tube (i.d. 0.13 mm and o.d. 1.6 mm, Supelco, Bellefonte, Pa.). Approximately 0.5 cm long piece of the Ag wire is exposed at tip 18. This exposed region was chloridized with a 1M HCl solution containing 0.1M $FeCl_3$.

The insulating sheath 20 around the inner Ag/AgCl electrode must be used to minimize the electrical noise during high-speed rotation. The tubing prevents any electrical contact between the inner Ag wire and the rotator. In addition, the internal reference electrode needs to be mechanically isolated from the rotator to avoid any vibration coupling from the rotator.

An external reference electrode 21, which in this specific embodiment is a 1 mm diameter silver wire chloridized with solution of a 1M HCl containing 0.1M $FeCl_3$, is connected electrically with a voltmeter 22, as is internal electrode 17, for measuring the potentiometric response of the electrode assembly.

Experimental Results

Potentiometric Measurements

The EMF responses of the rotating polyion-sensitive electrodes described hereinabove were measured at ambient temperature (~23° C.) via a Macintosh IIcx computer equipped with a LAB-MIO-16XL-42 16 bit A/D I/O board (National Instruments, Austin, Tex.) and VF-4 electrode interface module (World Precision Instruments, Sarasota, Fla.), controlled by LabView 2 software (National Instruments, Austin, Tex.).

Heparin Concentration Measurements via Continuous Protamine Titration

Titrations of 0.05 U/ml heparin in 3 ml buffer (50 mM Tris-HCl, pH 7.4, containing 0.12 M NaCl) were carried out by continuous infusion of 0.1 mg/ml protamine aqueous solution with a syringe pump (model MD-1001, BAS Inc., West Lafayette, Ind.), at a infusion rate of 5 μl/min. The titrations were monitored with a protamine-sensitive electrode that was either rotating (3000 rpm) or static. A stir bar was used in the static electrode experiments to achieve rotational solution phase convection. Blank titration curves for protamine-sensitive electrodes (static and rotating ones) were also recorded with continuous protamine infusion into a buffer solution (0 U/ml heparin) under the same experimental conditions. Results were averaged and the confidence intervals were calculated using the Student's t-test at the 95% confidence level.

Figure 2A:
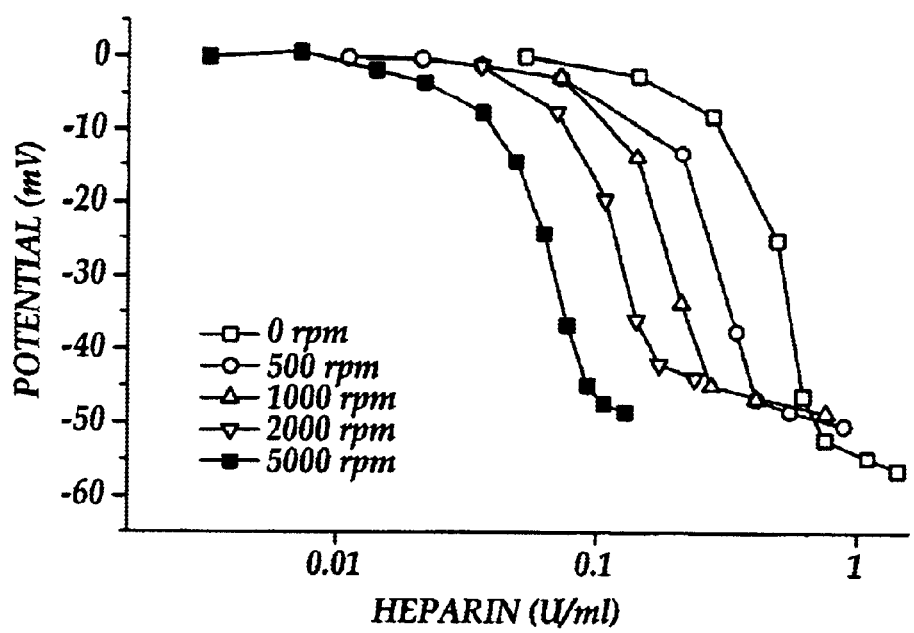
FIG. 2(a) is a graphic representation of heparin calibration curves obtained with a rotating heparin-sensitive electrode.
Figure 3A:
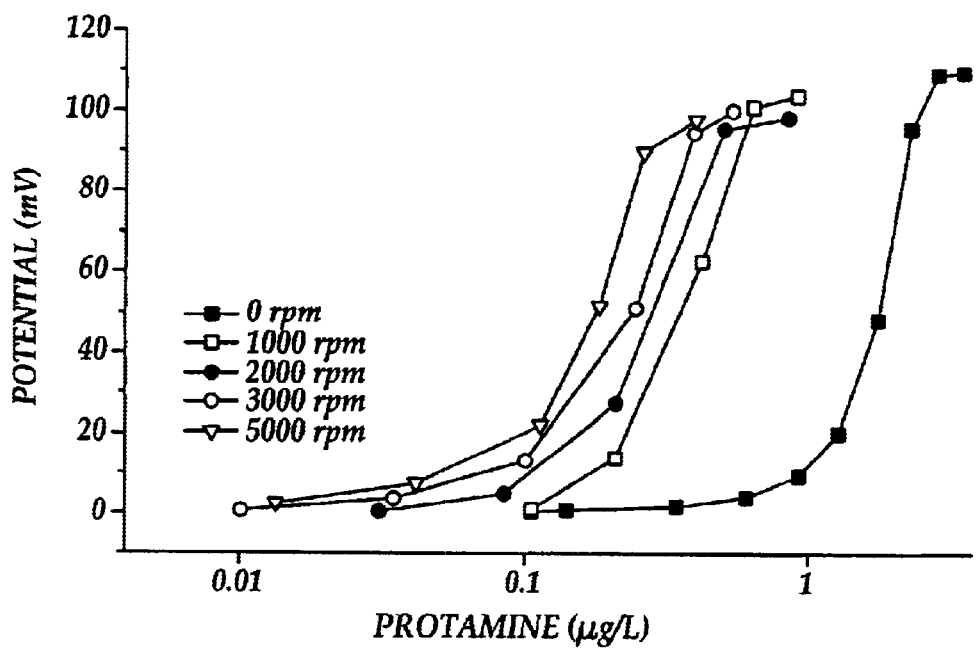
FIG. 3(a) is a graphic representation of protamine calibration curves obtained with a rotating protamine-sensitive electrode.

FIG. 2(a) is a graphic representation of polyanionic heparin calibration curves obtained with a rotating heparin-sensitive electrode in Tris buffer (50 mM Tris and 0.12 M NaCl) at different rotation speeds. Also shown is the response observed when the electrode is not rotated (0 rpm), but the sample is mixed using a conventional stir-bar. Obviously, the potentiometric response curves are shifted toward much lower concentrations by rotating the membrane electrode. Specifically, without rotation, the lower limit of detection (LLOD), defined as the polyion concentration that yields an average ΔEMF value from background buffer signal of ±3 mV (+ in the case of polycation measurements; − in the case of polyanion measurements), is approximately 0.1 U/ml. However, with rotation at 5000 rpm, the LLOD was lowered to 0.01 U/ml, a ten-fold improvement. A similar effect was observed for the response of the polycation-sensitive electrode toward protamine (see, FIG. 3(a)), where rotation at 6000 rpm yields a detection limit of 0.02 μg/ml.

Figure 2B:
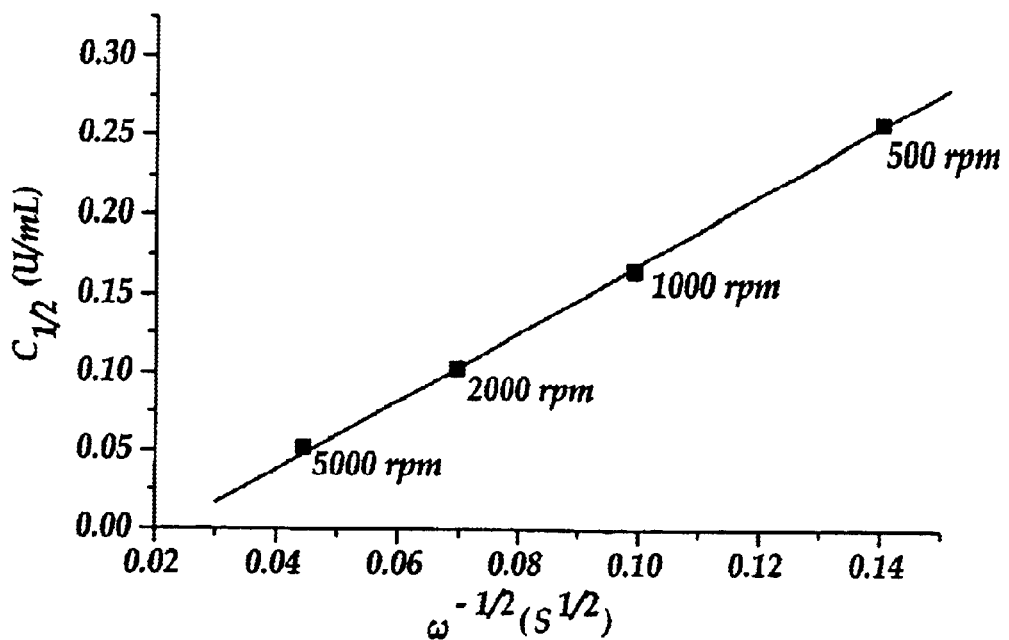
FIG. 2(b) is a graphic representation of the relationship between measured $C_{1/2}$, the polyanion concentration corresponding to one-half the total maximum ΔEMF response toward heparin, and $\omega^{-1/2}$, where ω is the rotation angular frequency.

In addition, by defining the polyion concentration that corresponds to the ΔEMF that is half of the total maximum ΔEMF (maximum occurs when sample concentration of polyion is high enough to achieve full equilibrium at membrane/sample interface) as $C_{1/2}$, which is proportional to the LLOD, a linear relation was found between $C_{1/2}$ and $\omega^{-1/2}$ for both the polyanion and polycation sensors as shown in FIG. 2(b) and FIG. 3(c) which are graphic representations of the relationship between measured $C_{1/2}$ toward heparin or protamine, respectively, and $\omega^{-1/2}$, where ω is the rotation angular frequency.

This linear relation can be theoretically predicted by inserting Eqn. 2 into Eqn. 1. Thus, the improvement in sensitivity with increasing rotation speed is the result of a decrease in diffusion layer thickness, not an artifact resulting from a possible change in the three-dimensional structure of protamine or heparin (i.e., uncoiling or unfolding) caused by the vigorous hydrodynamic convection.

A direct comparison of the mass transfer of polyion to the surface of the membrane for the two hydrodynamic cases (stir bar convection vs. rotating the electrode) can also be made by determining the rotation speed required to achieve the same LLOD value for the two configurations. Indeed, in the case of protamine measurements with the polycation-sensitive membrane electrode, it has been found that the rotated electrode has the same LLOD as when convection occurs by stirring when the rotation speed is 250 rpm (data not shown). Assuming a kinematic viscosity of $10^{-6}$ $m^2s^{-1}$ for the aqueous test solution and an aqueous phase diffusion coefficient for protamine of $5\times10^{-7}$ $cm^2/sec$, the equivalent diffusion layer thickness corresponds to 11.6 $\mu m$.

In principle, since the sensitivity (as indicated by $C_{1/2}$) is controlled by the rotation speed, additional lowering of the LLOD should be possible by further increasing the rotation speed. However, because $C_{1/2}$ is proportional to $\omega^{-1/2}$ rather than to $\omega^{-1}$ itself, further increasing the rotation speed above 6000 rpm will not significantly decrease the value of $\omega^{-1/2}$. Additionally, the mechanical noise becomes much more substantial at rotation speeds above 6000 rpm. Therefore, there is no analytical advantage gained by attempting to operate the PSEs of the illustrative embodiments at rotation speeds above this value.

Figure 3B:
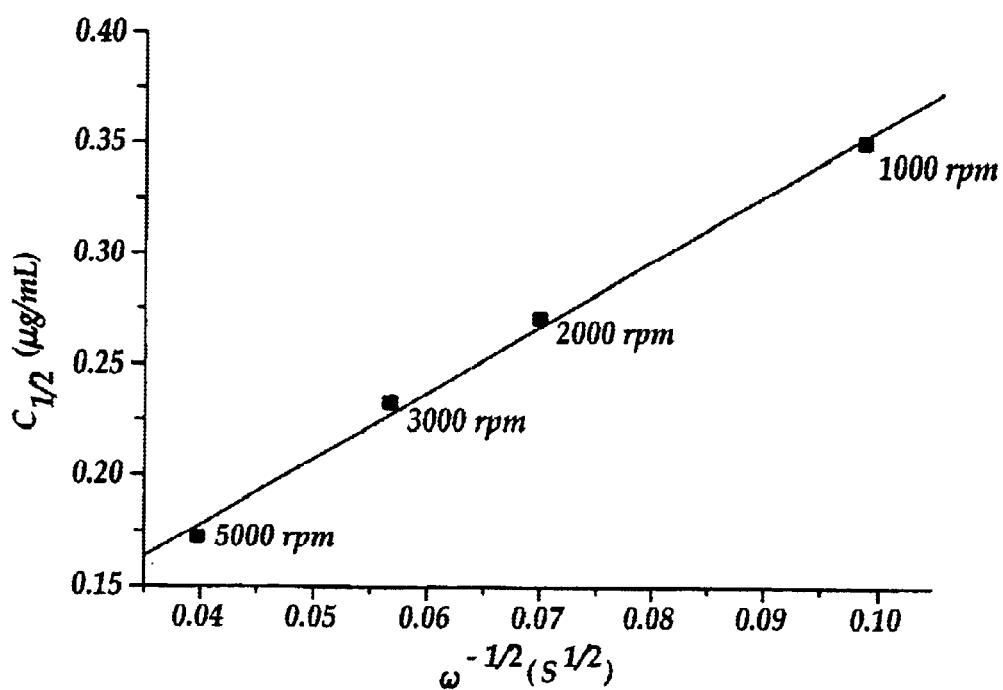
FIG. 3 (b) is a graphic representation of the relationship between measured $C_{1/2}$, the polycation concentration corresponding to one-half the total maximum ΔEMF response toward protamine, and $\omega^{-1/2}$, where ω is the rotation angular frequency.

The improved sensitivity achieved by rotating the PSEs can also be applied to detect lower concentrations of a polyionic species when titrated with another species. Indeed, for real sample measurements with PSEs, titrations are advantageous, since the steady-state EMF responses shown in FIGS. 2 and 3 are also dependent on the background cation or anion activities in the sample solution. In biological samples, for example, sodium and potassium ions are typically present in the case of polycation sensors and chloride ions are typically present in the case of anion sensors. Indeed, more reliable analytical results for measurement of polyion levels in complex samples, including whole blood, have been achieved by carrying out such potentiometric titrations with a rotating polyion-sensitive electrode.

Figure 4A:
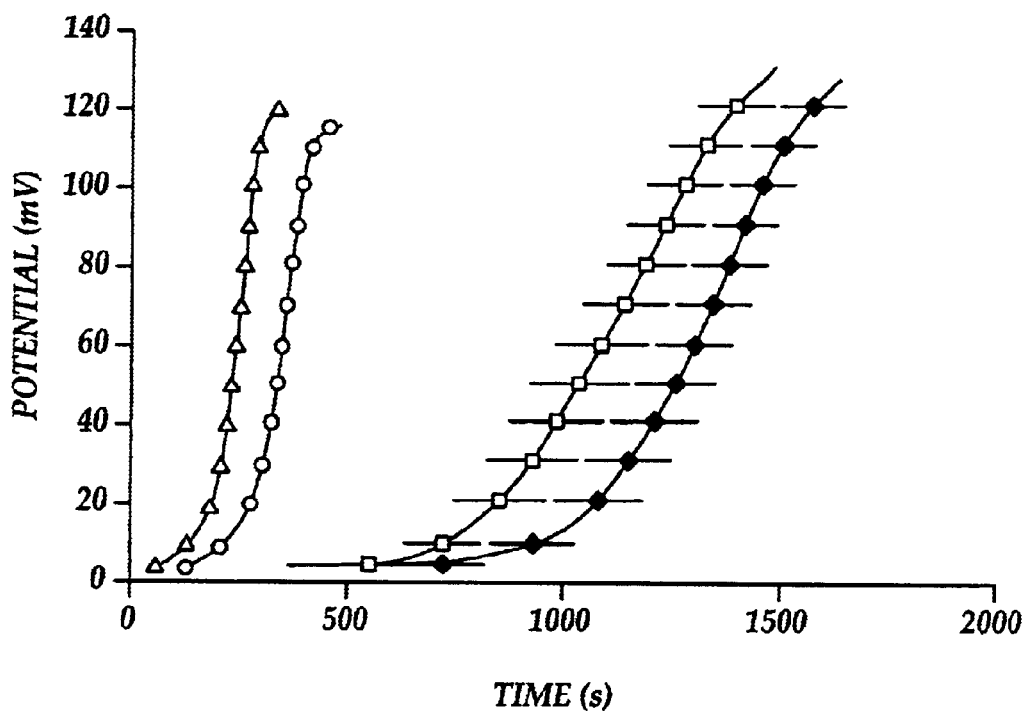
FIG. 4(a) is a graphic representation of the potentiometric data for the continuous infusion titration of 0.05 U/ml heparin in 3 ml buffer (50 mM Tris-HCl, pH 7.4, and 0.12 M NaCl) with 0.1 mg/ml protamine at a speed of 5 μl/min. (Δ) blank titration (0 U/ml heparin) with 3000 rpm rotating protamine-sensitive electrodes (the average of four titrations±confidence interval); (○) titration of 0.05 U/ml heparin using 3000 rpm protamine-sensitive electrodes as indicators (the average of four titrations±confidence interval is shown); (□) blank titration (0 U/ml heparin) with non-rotating protamine-sensitive electrodes (the average of six titrations±confidence interval is shown); and (♦) titration of 0.05 U/ml heparin using non-rotating protamine-sensitive electrodes (the average of six titrations±confidence interval is shown)

FIG. 4(a) is a graphic representation of the average (± confidence interval at 95% level with respect to time axis) potentiometric data for at least 4 separate continuous infusion titrations of 0.05 U/ml heparin in 3 ml Tris buffer with 0.1 mg/ml protamine at a speed of 5 ml/min symbolized as follows: (Δ) blank titration (0 U/ml heparin) with 3000 rpm rotating protamine-sensitive electrodes; (○) titration of 0.05 U/ml heparin using 3000 rpm protamine-sensitive electrodes as indicators; (□) blank titration (0 U/ml heparin) with non-rotating protamine-sensitive electrodes; and (◆) titration of 0.05 U/ml heparin using non-rotating protamine-sensitive electrodes.

Although 0.05 U/ml of heparin can be distinguished statistically from the blank using the non-rotating PSE as the end-point indicator, much greater precision in the titration data is obtained using the more sensitive rotating protamine PSE as shown in FIG. 4(a). Indeed, FIG. 4(b), which is an expanded time scale view of the titration data shown in FIG. 4(a) for the rotating electrode further illustrates the dramatic enhancement in precision that is achieved. Given this improved precision, it appears that levels of heparin down to 0.01–0.02 U/ml could easily be resolved from the blank by titration using a rotating PSE as the indicator electrode.

In addition, as shown in FIG. 4(a), much more rapid titrations can be completed owing to the improved detection limits of the rotating PSE design. In contrast, to increase the titration speed of a static PSE, one must increase the infused protamine concentration to 1 mg/ml (using the same flow rate). It was discovered, however, that at such high concentrations of titrant, even 0.1 U/ml heparin could not be distinguished statistically from the blank (results not shown).

Figure 4B:
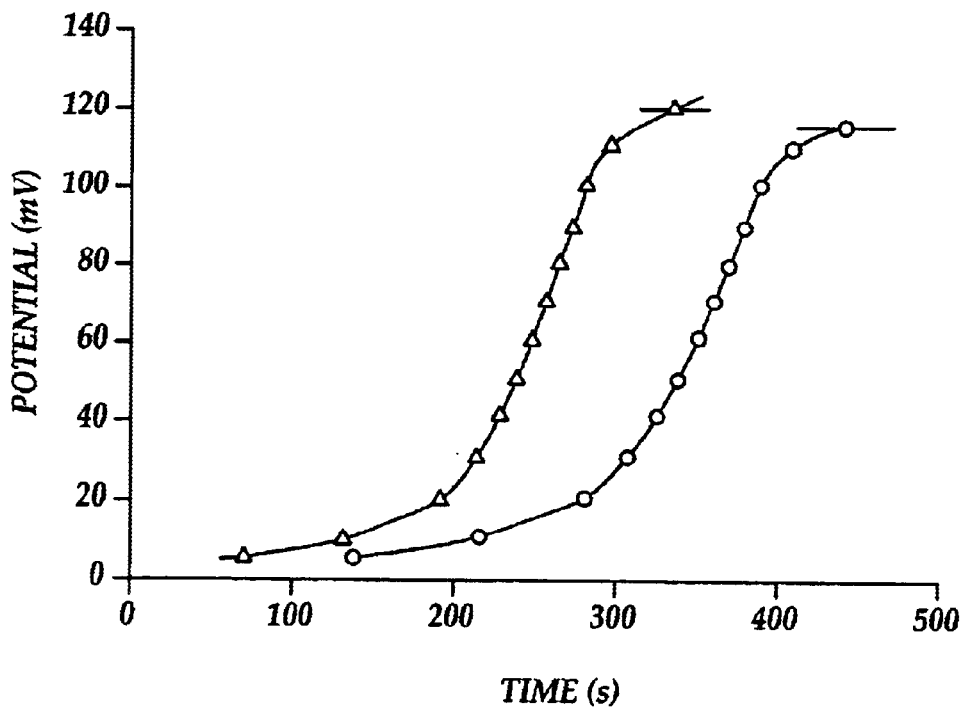
FIG. 4(b) is an expanded time scale view of the titration data shown in FIG. 4(a) for blank and titration of 0.05 U/ml of heparin carried out using rotating protamine PSE.

It should be noted that in previous electrochemical experiments, it was found that 1 unit of heparin requires about 10 $\mu g$ of protamine for neutralization when conducting manual titrations of heparin. In the experiments conducted with the rotating electrode configuration, as shown in FIG. 4(a) and FIG. 4(b), a total amount of 0.15 U heparin (0.05 U/ml of heparin in 3 ml buffer) was titrated with 0.1 mg/ml protamine at a speed of 5 $\mu l/min$. For the rotating electrode experiment, the time difference between $C_{1/2}$ of the blank and that containing 0.15 U heparin is 104.0±5.3 sec, i.e., the infused protamine at this endpoint is 0.1 mg/ml×5 $\mu l/min$× 104±5.3 sec=0.867±0.044 $\mu g$ protamine, or 5.78±0.29 $\mu g$ protamine/unit of heparin. This is less than the previously reported stoichiometry between protamine and heparin (~10 $\mu g$ protamine/unit of heparin). This difference is likely due to the combination of using continuous infusion of protamine to achieve the titration, as compared to the single point manual titrations, coupled with the enhanced mass transfer that occurs due to the use of the rotating electrode design. In effect, the binding between protamine and heparin is not rapid enough to reach equilibrium before some of the added protamine is extracted into the membrane of the electrochemical detector to yield a potentiometric response. This kinetic effect on the observed stoichiometry is consistent for increasing low concentrations of heparin detected (0.05–0.5 U/ml) by the titration and can thus be calibrated out for quantitative determinations of heparin using the rotating electrode configuration.

Beyond improvements in detection limits and precision as demonstrated in the experiments described hereinabove using 3 ml sample volumes, the use of rotating PSEs may also be advantageous from the standpoint of achieving more reproducible results in small sample volumes (<1 ml). Obtaining reproducible polyion potentiometric responses in small sample volumes using conventional stir-bars is quite difficult, owing to variations resulting from stir bar position, inter alia, that can affect polyion mass transfer and, hence, the observed EMF response. However, rotating the electrode rather than stirring the bulk of the sample phase could potentially make measurements in sub-ml volumes quite easy and reproducible.

In summary, the novel rotating polyion-sensitive membrane electrodes disclosed herein have the ability to lower the detection limits of PSEs significantly. A ten-fold sensitivity improvement is easily achieved at modest rotation speeds of between about 5,000–6,000 rpm. The detection limits for planar heparin and protamine sensitive membrane electrodes evaluated in the rotating electrode configuration are also lower than the previously reported cylindrical electrode designs used with conventional stirring to effect mass transfer of the polyion. When measuring low concentration of analyte polyions via titration (e.g. with protamine) using polyion-sensitive electrodes as end-point indicators, more precise results and analytical resolution can be obtained with the rotating polyion-sensitive electrodes. Given these results, the rotating electrode configuration is an attractive tool for measuring low levels of biologically important polyions in clinical samples. Moreover, the ability to use rotating PSEs in small sample volumes is advantageous in bioimmunoassays, such as recently developed non-separation, electrochemical immunoassays, where the antibodies and other reagents (including synthetic polyion label) are extremely expensive.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention and should not be construed to limit the scope thereof.

What is claimed is:

1. A potentiometric polyionic membrane electrode assembly, comprising:
   a rotatable generally cylindrical housing having a bore through the central axis thereof;
   a rotator configured to rotate the housing;
   a polyion-responsive membrane of a polymeric matrix material which has a non-equilibrium potentiometric response mechanism disposed on one end of the housing so as to be rotatable with the housing and to seal a reference solution inside the housing and to contact a sample solution external to the housing, wherein the membrane rotation improves mass transfer of polyion to the membrane surface;
   an internal reference electrode extending through the bore of the housing and being arranged so that one end of the internal reference electrode is disposed in the internal reference solution, the internal reference electrode being insulated from the housing; and
   an external electrode.

2. The potentiometric polyionic membrane electrode assembly of claim 1 wherein the polyion-responsive membrane comprises, in admixture, a polymeric matrix material, lipophilic cation- or anion-exchange material, and, optionally, a plasticizer, the electrode membrane admixture formulation being selectively responsive to cationic or anion macromolecules, respectively.

3. The potentiometric polyionic membrane electrode assembly of claim 2 wherein the electrode membrane admixture is selectively responsive to cationic macromolecules.

4. The potentiometric polyionic membrane electrode assembly of claim 3 wherein the cationic macromolecules is protamine.

5. The potentiometric polyionic membrane electrode assembly of claim 2 wherein the electrode membrane admixture is selectively responsive to anionic macromolecules.

6. The potentiometric polyionic membrane electrode assembly of claim 5 wherein the anionic macromolecule is heparin.

7. The potentiometric polyionic membrane electrode assembly of claim 1 wherein the polyion-responsive membrane is planar.

8. A method of measuring the concentration of a polyionic macromolecule in a liquid medium as a function of its potentiometric response, the method comprising:
   (a) bringing a polyion-responsive membrane electrode into contact with the liquid medium containing an unknown quantity of polyionic macromolecule analyte, the polyion-responsive membrane comprising a polymeric matrix material which baa a non-equilibrium potentiometric response mechanism to the analyte;
   (b) rotating the polyion-responsive membrane in the liquid medium, wherein the membrane rotation improves mass transfer of the polyionic macromolecule to the membrane surface; and
   (c) measuring a potentiometric response which is indicative of the concentration of analyte in the liquid medium.

9. The method of claim 8 wherein the polyion-responsive membrane is rotated at speeds ranging from about 500 rpm to 6000 rpm.

10. The method of claim 9 wherein the polyion-responsive membrane is rotated at 5000 to 6000 rpm.

11. The method of claim 8 wherein the polyion-responsive membrane is planar.

* * * * *